United States Patent [19]

Hill

[11] Patent Number: 5,417,576

[45] Date of Patent: May 23, 1995

[54] MEANS AND METHOD FOR MICROBIOLOGICAL GROWTH AND IN SITU OBSERVATION WITH MICROSCOPES

[75] Inventor: Dennis R. Hill, Urbandale, Iowa

[73] Assignee: Iowa Methodist Medical Center, Des Moines, Iowa

[21] Appl. No.: 151,291

[22] Filed: Nov. 12, 1993

[51] Int. Cl.$^6$ .................. C12M 3/04; C12M 1/16; C12M 1/20

[52] U.S. Cl. ................... 435/299; 435/285; 435/287; 435/293; 435/297; 435/298; 435/301; 220/306; 220/309; 220/352; 359/398

[58] Field of Search .............. 435/287, 293, 299, 301, 435/284, 285, 297, 298; 220/306, 309, 352; 359/398

[56] References Cited

U.S. PATENT DOCUMENTS

| | | | |
|---|---|---|---|
| 3,491,913 | 1/1970 | Giraudet et al. | 220/352 |
| 3,729,382 | 12/1970 | Shaffer et al. | 19/13 |
| 3,888,741 | 6/1975 | Freake et al. | 435/301 |
| 4,271,270 | 6/1981 | Lukacsek | 43/29 |
| 4,280,000 | 7/1981 | Kozak, Jr. et al. | 43/24 |
| 4,280,002 | 7/1981 | Bailey et al. | 43/29 |
| 4,299,921 | 11/1981 | Youssef | 43/29 |
| 4,321,330 | 3/1982 | Baker et al. | 43/29 |
| 4,587,213 | 5/1986 | Malecki | 43/3 |
| 4,668,633 | 5/1987 | Walton | 43/29 |
| 4,728,607 | 3/1988 | Dorn et al. | 43/3 |
| 4,790,640 | 12/1988 | Nason | 35/53 |
| 4,974,952 | 12/1990 | Focht | 35/53 |
| 4,978,507 | 12/1990 | Levin | 435/301 |
| 5,134,064 | 7/1992 | Nordlund | 435/299 |

OTHER PUBLICATIONS

Davise H. Larone, "Medically Important Fungi-A Guide To Identification" 2d Edition 1987 (pp. 180-181) Elsevier Scientific Publishing, New York.

*Primary Examiner*—William H. Beisner
*Assistant Examiner*—Jane Williams
*Attorney, Agent, or Firm*—Zarley, McKee, Thomte, Voorhees & Sease

[57] ABSTRACT

Devices and methods for both growing and in situ observation of microbiological cultures. The devices utilize thin transparent surfaces which bound a thin chamber which holds a layer of agar or the like and the microbiological sample. The agar and sample can be deposited through a sealable opening into the container. The dimensions of the container are such that it can be placed in a microscope allow in situ viewing of the culture through top or bottom surfaces. The method according to the invention fosters improved culture growth in the thin chamber and allows in situ observation of the culture with a conventional microscope.

22 Claims, 3 Drawing Sheets

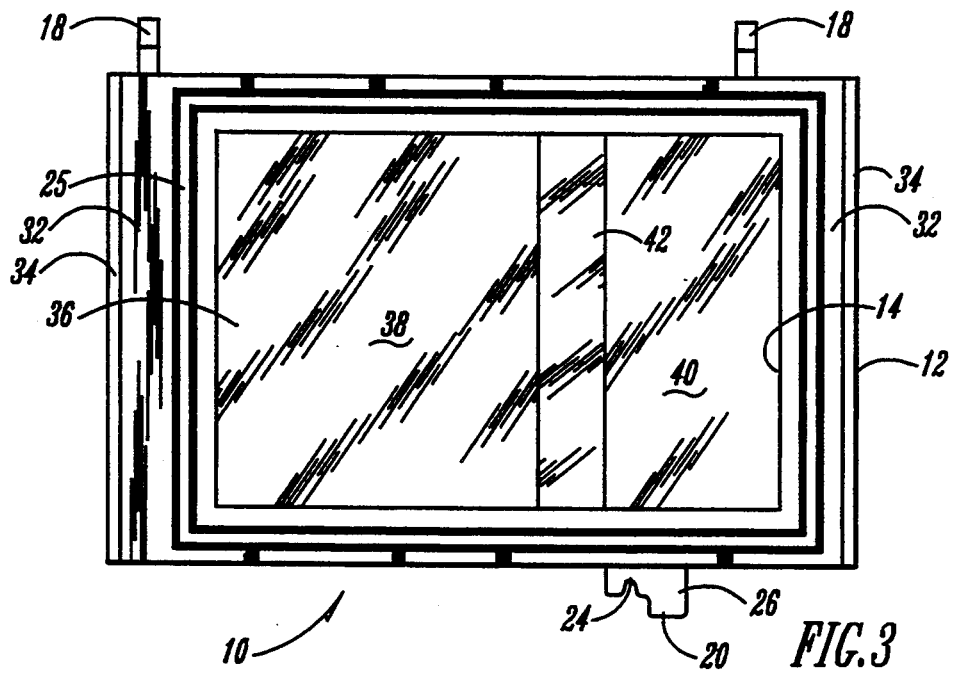
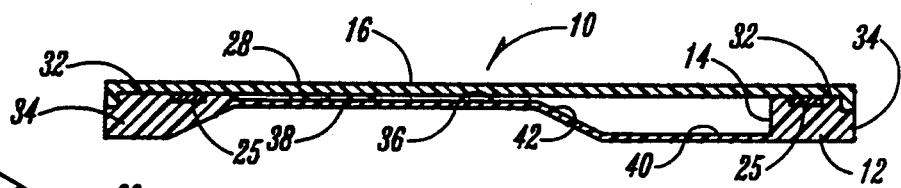
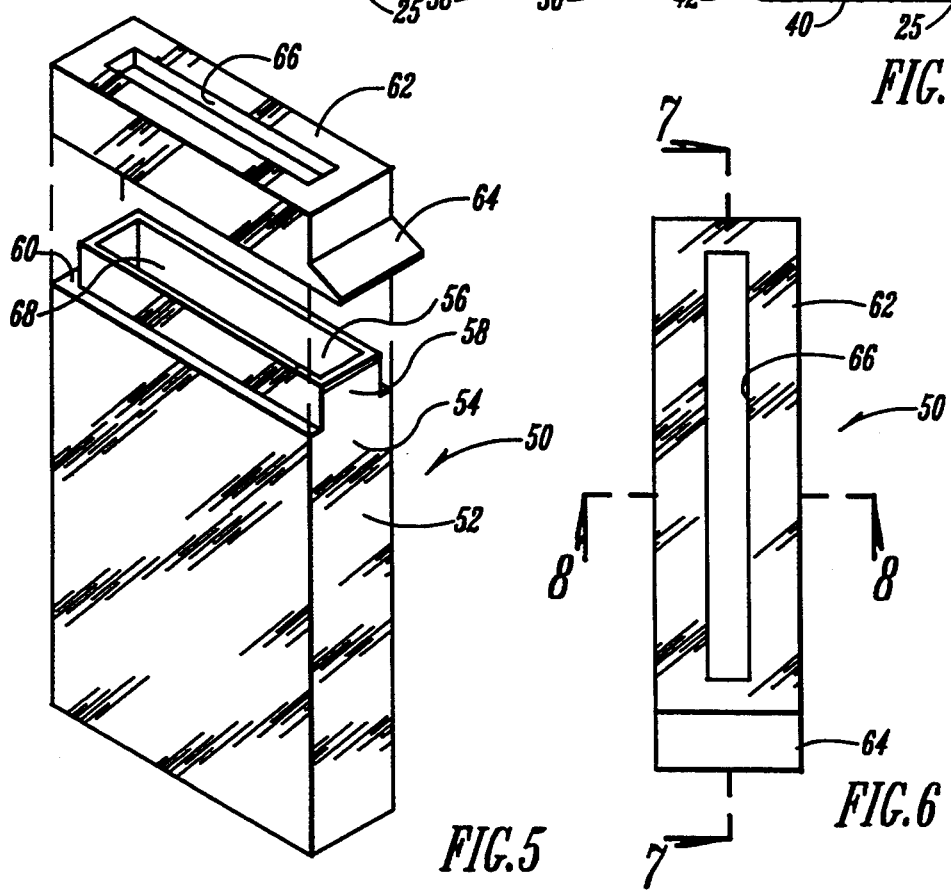

MEANS AND METHOD FOR MICROBIOLOGICAL GROWTH AND IN SITU OBSERVATION WITH MICROSCOPES

BACKGROUND OF THE INVENTION

A. Field Of The Invention

The present invention relates to methods and containers for growing microscopic sized microorganisms and, in particular, to methods and structures for not only growing microbiological matter, but also microscopic viewing of the same without removal from the container.

B. Problems in the Art

Presently, the conventional way to grow microbiological organisms in a controlled and observable manner is to utilize such things as petri dishes, tissue culture flasks, tissue culture slide chambers, and fungus isolation bottles. These terms, and the associated structures defined by these terms, are well known in the art.

There are a variety of reasons for growing such organisms. Some examples include testing human tissue for the presence of unhealthy microorganisms, creating microorganisms for research, testing, or designated use, determining the presence of microbiological activity, etc.

Useful growth generally must be in these types of structures. It is not a trivial matter to generate growth. Such things as agar or other known in the art substances are used in the containers to instill a base or environment that is conducive to such growth. Also, the environment itself must be somewhat carefully controlled.

Another more subtle aspect is as follows. These structures and techniques are sometimes used to handle what might be considered dangerous microorganisms from a health risk standpoint. Thus, most of these structures are sealable from the external surroundings and allow for careful handling of these growths, and any airborne particles associated with the growth.

It is one matter to grow the microbiological activity. It is another matter to be able to detect the growth and identify it. These microorganisms are very small and generally require observation under microscopes to validate their identification.

Conventionally, the tasks of first growing the microorganisms and then viewing them under microscopes are done with two different structures. The petri dishes, tissue culture flasks, and fungus isolation bottles, represent structures to grow the items in the above discussed controlled manner. The prevailing view is that a substantial amount of agar or the like is required to stimulate valid and complete growth. Therefore, petri dishes and the like tend to be relatively large and deep, with a large access through a large cover or the like to allow introduction of agar, and then placement of a plurality of samples in various locations within the structure, such as the dish.

Examples of these types of structures can be found in the following U.S. Pat. Nos.:

| U.S. PAT. NO. | INVENTOR |
| --- | --- |
| 3,729,382 | Shaffer, et al. |
| 4,299,921 | Youssef |
| 5,134,064 | Nordlund |
| 4,668,633 | Walton |
| 4,280,002 | Bailey, et al. |
| 4,587,213 | Malecki |

-continued

| U.S. PAT. NO. | INVENTOR |
| --- | --- |
| 4,280,000 | Kozak, Jr. et al. |
| 4,728,607 | Dorn, et al. |

A similar device that is specifically used to culture tissue samples is shown at:

| U.S. PAT. NO. | INVENTOR |
| --- | --- |
| 4,321,330 | Baker, et al. |

While these types of devices are generally considered by those in the art to be advantageous for growing microbiological activity, a distinct disadvantage is that they generally can not be utilized to also view the contents in situ under conventional light microscopes. The structures or containers are simply too large, and primarily too thick, to be positioned under and held in place by calibers of standard microscopes. Also, they generally are not conducive to good viewing because of their thickness, and the thickness of the agar or other growth medium in the container.

Microscope viewing of the growth inside these structures is therefore generally carried on as follows. The container is opened, and a portion of the growth is removed and placed onto a microscope slide. The slide is thin, transparent, and therefore allows precise viewing of the microbiological activity under conventional microscopes, as well as allows placement of the slide in the calibers.

Conventional laboratory microscope slides are well known in the art. Examples of more exotic types of structures for viewing in microscopes can be found in the following U.S. Pat. Nos.:

| U. S. PAT. NO. | INVENTOR |
| --- | --- |
| 4,790,640 | Nason |
| 4,271,270 | Lukacsek |
| 4,974,952 | Focht |

While such a system (growth in one container, microscope viewing by placing a sample on an microscope slide) is held by the state of the art to work adequately, problems, deficiencies, and room for improvements are submitted to yet exist with that process.

First, current practices, which utilize relatively thick, large amounts of agar as the growth medium, translate into relatively long amounts of time for growth to occur.

Second, once growth has occurred, the time consuming and cumbersome procedures of transferring a portion of the growth to a microscope slide (including all the preparation and handling that goes with this) must be done. Such a process must be done each time the cultured growth is checked.

Third, such handling introduces a level of disruption, destruction, and therefore uncertainty to the culture sample. No in situ microscopic viewing of the culture can take place.

A discussion of conventional techniques for microscoping examination of growth such as fungus is set forth at pages 180-181 of "Medically Important Fungi—A Guide to Identification" by Davise H. Larone (1987). At those pages, three types of microscopic examination techniques are set forth, first what is called a tease mount—which involves tearing a small portion of the growth from an agar surface and placing it in a drop off lactophenol cotton blue (LPCB) on a clean glass slide, covering that portion with the cover slip, and observing it under a microscope. It is a rapid method but is destructive and does not always preserve the original position and structure of the conidia, spores and the like; which are extremely important to allow accurate identification. The second method is called cellophane tape mount and is also rapid. It involves using the tape to remove part of the growth. The tape is then placed on a small drop of LPCB on a glass slide, sticky side down, and examined under a microscope. This method is better at retaining the original position of characteristic fungal structures. Third, what is called the slide culture technique is stated to be the best method for preserving and observing the actual structure of a fungus in a slide culture. Its disadvantages include that it is not rapid, it is described, however, as unsurpassed as a routine means of studying the fine points of microscopic morphology of fungi. The method includes suspending a microscopic slide in a petri dish with a 4 mm deep, 1×1 cm block of agar on top of the slide. The specimen is inoculated on the four sides of the agar block and a cover slip is placed over the block. Water is placed in the bottom of the dish and the specimen is incubated at room temperature. Fungus will ordinarily grow on the surface of the slide and under the surface of the cover slip. It is checked periodically and when growth is discovered, the cover slip is removed and placed in a drop of LPCB on a second slide. The agar block can also be removed from the first slide and a cover slip placed over that area. Both slides can then be viewed under a microscope.

It can therefore be seen that conventional examination techniques either sacrifice accuracy of identification for speed or speed for accuracy of identification. The most accurate method, the slide culture method, does not allow in situ viewing and is slow. It also utilizes a thick piece of agar.

There is, therefore, a need in the art for an improvement in this field. It is therefore a primary object of the present invention to provide a means and method for microbiological growth and in situ observation with microscopes which improves upon the state of the art.

Another object of the present invention is to provide an invention as above described which provides a growth chamber and the ability to view the chamber with a microscope, which is also flexible and versatile with respect to these procedures.

Another object of the present invention is to provide a means and method as above described which reduces the resources needed in these types of procedures in terms of time and effort.

A still further object of the present invention is to provide a means and method as above described which reduces the time needed to adequately grow the cultures to a point where they are useful.

Another object of the present invention is to provide a means and method as above described which reduces the time required to handle the cultures.

Another object of the present invention is to provide a means and method as above described which reduces the time required to identify the culture.

Another object of the present invention is to provide a means and method as above described which can eliminate laborious and time consuming tasks associated with such procedures.

A still further object of the present invention is to provide a means and method as above described which eliminates the need for or use of different structures and procedures for growth and observation of the cultures.

Another object of the present invention is to provide a means and method as above described which increases the accuracy and speed of growth and identification of cultures.

Another object of the present invention is to provide a means and method as above described which allows access to the culture without substantial disruption or destruction of the culture.

Another object of the present invention is to provide a means and method as above described which increases the number and type of procedures and options available to be performed on the culture.

Another object of the present invention is to provide a means and method as above described which increases the observability of the culture, for example, allowing in situ microscopic observation, in certain circumstances from more than one side, as well as allowing better non-microscopic observation.

A still further object of the present invention is to provide a means and method as above described which increases safety as to handling of such cultures.

Another object of the present invention is to provide a means and method as above described which simplifies and increases flexibility with respect to sub-culturing of cultures.

These and other objects, features, and advantages of the present invention will become more apparent with reference to the accompanying specification and claims.

SUMMARY OF THE INVENTION

The present invention pertains to apparatus and methods for culturing microbiological activity and observing those cultures. The apparatus includes a container having a thin profile which can itself be positioned and held in a conventional microscope. The container includes a thin chamber which can hold a thin layer of agar or the like. The container, having transparent walls and chamber are thin enough so that the culture can be viewed in a microscope, yet of sufficient dimensions that culture can satisfactorily grow in the manner that is useful for identification, or for other purposes that may be desired.

The container generally has an access opening to the chamber which is big enough to allow such options as the introduction of a cover slip, such as known in the art, removal of samples, and the initial preparation of the chamber by the addition of agar or the like in a controlled, predictable manner. The opening is sealable and the entire container can be secured for handling.

One optional feature of the apparatus is the provision of a chamber having various thicknesses. The agar, and thus the microbiological activity at various locations, can be observed relative to various thickness of agar (or the like) between top and bottom chamber boundaries.

The method according to the present invention includes the steps of creating at least a portion of the growth medium, such as agar, into a thin layer on top of a transparent surface. Another top transparent surface is closely adjacent or directly abuts the agar and microbiological activity. This combination allows the growth of the culture and observation of the same at any time in a conventional microscope. In certain circumstances, in situ viewing of two sides of the growth is possible.

Optional features include growing the sample in a growth medium of varying thicknesses.

Other features, options and advantages are possible as described elsewhere in this description.

BRIEF DESCRIPTION OF THE DRAWINGS

FIG. 3 is a top plan view of the embodiment of FIG. 1 but with the cover portion removed to show the bottom section only.

FIG. 4 is a sectional view taken along line 4—4 of FIG. 2.

FIG. 5 is a perspective view of a second embodiment according to the present invention, showing a removable cover portion in exploded fashion.

FIG. 6 is a top plan view of FIG. 5.

DETAILED DESCRIPTION OF PREFERRED EMBODIMENTS OF THE PRESENT INVENTION

A. Overview

Figure 1:
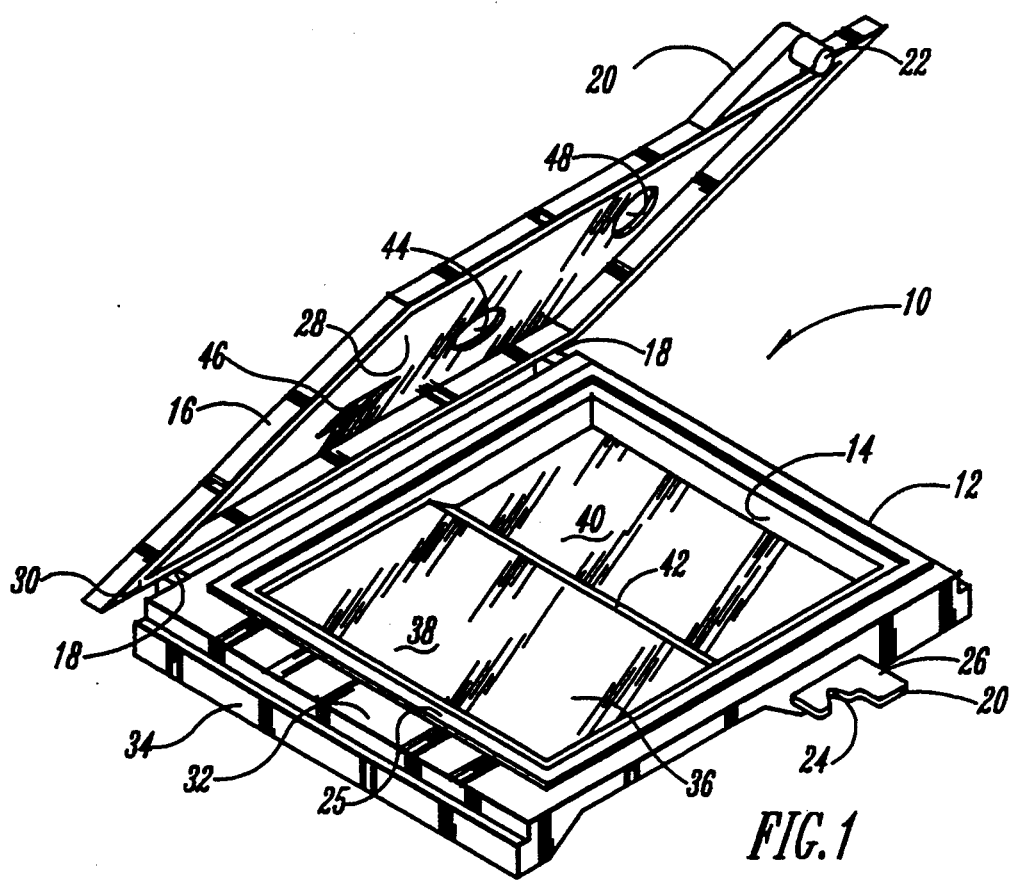
FIG. 1 is a perspective view of a preferred embodiment according to the present invention.

To assist in a better understanding of the invention, a detailed description of the preferred embodiments will now be set forth. It is to be understood that these are exemplary illustrations of several forms the invention can take and are not intended to specifically limit the scope of the invention.

The appended drawings will be referred to frequently in this description of the preferred embodiments. Reference numerals will be used to indicate certain parts and locations in the drawings. The same reference numerals will be used to indicate the same parts and locations in the drawings unless otherwise indicated.

B. General Structure and Methods as to All Embodiments

Three separate embodiments will be described. The first is shown at FIGS. 1-4; the second at FIGS. 5-8, and the third at FIG. 9. In each instance, a case or container which can be used for both culturing and in situ microscopic observation is disclosed. For purposes of simplicity, throughout the drawings, the entire device will be called a "case". The portion of the case where the agar and culture is grown will be called the "chamber". The chamber will be defined as being positioned in the "base" of the case. A "cover", also a part of the case, will be used to seal off the chamber.

Each of the embodiments are sized to fit within conventional light microscopes. This means that they are of thin overall thickness to be able to fit under the objective lens of the microscope as well as to be held by conventional calipers of microscopes. All walls of each embodiment are transparent; generally made out of some sort of transparent plastic. Other materials are possible.

The length and width dimensions of each embodiment, however, can vary. Generally, they are about 60 mm to 70 mm by 80 mm to 90 mm (2¼ by 3¼ inches) and approximately ¼" tall. The dimensions can vary, however. For example, outer dimensions in the preferred embodiment are primarily a function of being small enough to fit under the objective lens and within the calipers of conventional microscopes. Therefore, the dimensions of the case (including thickness) can vary over a range of values, such as can be understood by those of ordinary skill in the art. In the preferred embodiments, a thickness of about 15 mm or less is preferred, with some styles being about 6 mm thick. It is further to be understood that one optional aspect of the preferred embodiments is utilizing an interior chamber of varying dimensions, including thickness. In the preferred embodiment, chamber thickness between about 1 mm and 4 mm was used. Other dimensions are possible. Furthermore, the preferred embodiments have generally rectangular shapes with perpendicular angles between abutting surfaces. Other shapes are possible.

The exact dimensions of the embodiments are not critical to their operation, except for the ability to fit into conventional light microscopes.

C. Embodiment One (FIGS. 1-4)

FIG. 1 shows a case 10 having a base 12 in which is defined a chamber 14. A cover 16 is attached by hinge 18 to base 12 along adjacent edges at what will be called the back of case 10.

What will be called a latch 20 includes a pin 22 that extends from cover 16, and which is received by and frictionally fits within a slot 24 in tab 26 attached to base 12. As can be easily understood, this arrangement, which is well known, would allow for a secure but releasable closure of cover 16 onto base 12.

As can be seen in FIG. 1, cover 16 has a flat surface 28 surrounded by an outer frame 30. In comparison, base has a raised frame 32 and shoulders 34. Raised frame 32 receives frame 30 of cover 16. Inner frame 32 of base 12 abuts flat surface 28 of cover 16 when it is hinged down into a covering relationship over chamber 14.

As can furthermore be appreciated, a gasket 25 or some sort of sealant could be placed between base 12 and cover 16 to create an airtight sealing of chamber 14 by case 10.

FIG. 1 also shows that base 12 includes surface 36 upon which the agar and culture is placed; and which forms the bottom floor of chamber 14. In this preferred embodiment, surface 36 actually has two elevations. First elevation 38 (to the left in FIG. 1) is slightly higher than second elevation 40. A transition surface 42 links first and second elevations 38 and 40 and therefore is obliquely angled to the planes in which first and second elevations 38 and 40 reside. Such a structure therefore presents a chamber 14 with different or varying depth or thickness. In this embodiment, when cover 16 is closed onto base 12, it is approximately 6 mm thick at its thickest point(s). Chamber 14, however, is approximately 1 mm thick between cover 16 and first elevation 38, and 4 mm thick between cover 16 and second elevation 40.

Figure 2:
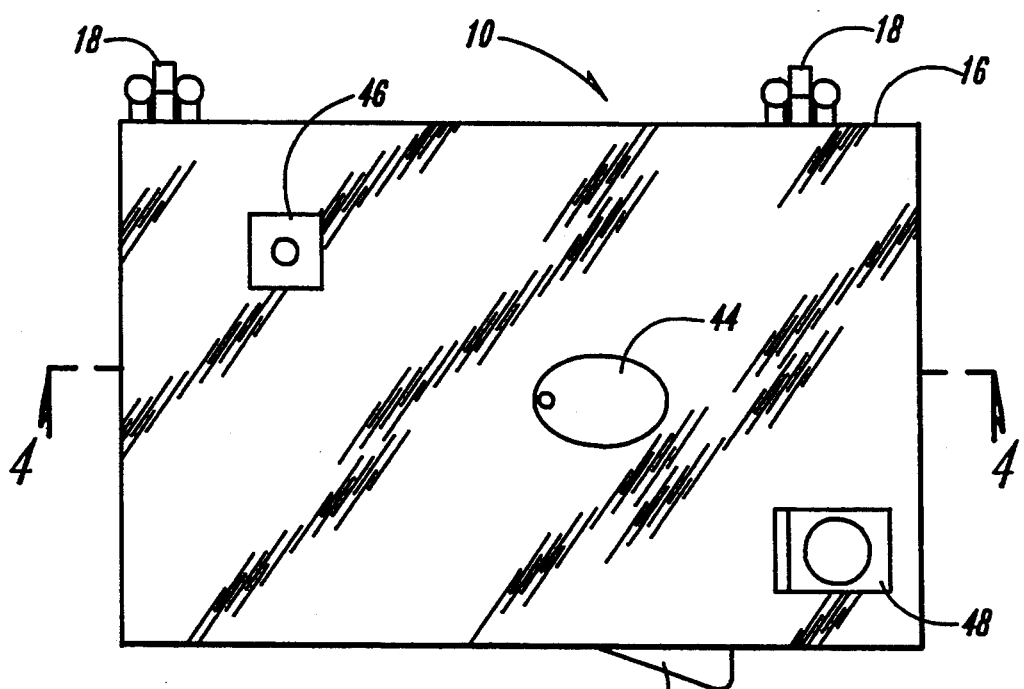
FIG. 2 is a top plan view of FIG. 1.

FIG. 2 shows a closed case 10 from the top. Case 10 allows features such as a stain port 46, air port 48, and a built-in coverslip 44 (an area of increased thickness in the cover). These features are well known in the art. Stain port 46 allows the introduction of special stains into the chamber 14 to help identification of the microbiological activity without unduly disturbing the contents.

Air port 48 allows periodic introduction of air to foster culture growth. A microbiological filter is generally included with the air port to prevent microbiological organisms from either entering or leaving chamber 14. As can be well understood by those of ordinary skill in the art, a standard cover slip (not shown) could be placed over any agar in base 12 and cover 16 closed down over such a coverslip, if desired.

FIG. 3 shows base 12 from the top with cover 16 removed. It shows the relationship of first and second elevations 38 and 40 for this particular embodiment. It is to be understood, however, that the exact dimensions of those portions can be altered. Furthermore, there could be three or more elevations if desired. Alternatively, the entire surface 36, or portions of it, could be sloped, instead of stepped, if desired.

FIG. 4 shows by cross-section the relationship between first and second elevations 38 and 40, and flat surface 28 of cover 16 when cover 16 is closed upon base 12. FIG. 4 illustrates how thin this embodiment is, which allows it to be placed in conventional microscopes. The growth can also be viewed from either side under a conventional microscope.

D. Embodiment Two (FIGS. 5–8)

FIG. 5 shows another embodiment for the invention; namely case 50. As can be seen, case 50 is basically a rectangular box made of transparent material. The base 52 of this embodiment is essentially a closed-off thin box with one end 54 having an opening 56 formed by an upwardly extending (from the perspective of FIG. 5) flange 58 surrounded on three sides by shoulder 60. Cover 62 fits over flange 58 and abuts against shoulder 60. Cover 62 includes a tab 64 which extends beyond the outer perimeter of base 52, which helps any handler of case 50 to remove cover 62.

FIG. 6 (in combination with FIG. 5), reveals that this embodiment also includes an indentation 66 in the top of cover 62.

Figure 7:
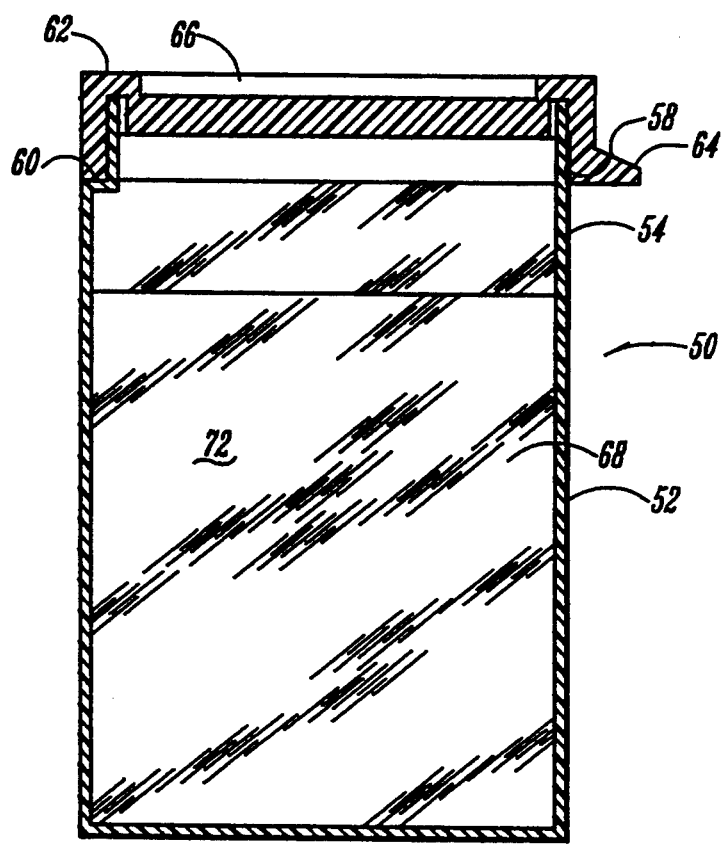
FIG. 7 is a sectional view taken along line 7—7 of FIG. 6.
Figure 8:
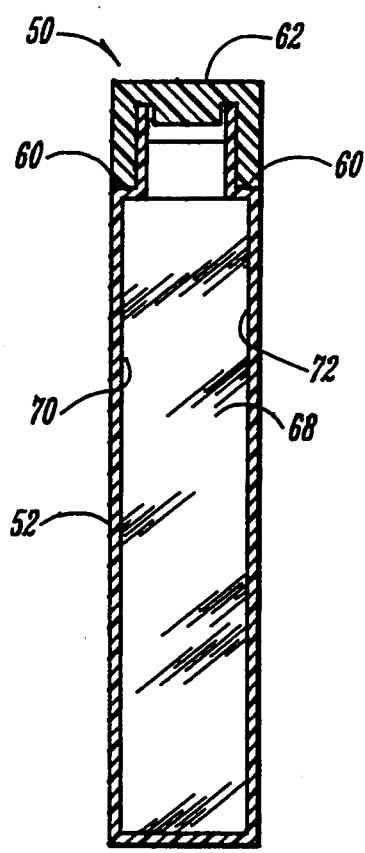
FIG. 8 is a sectional view taken along line 8—8 of FIG. 6.
Figure 9:
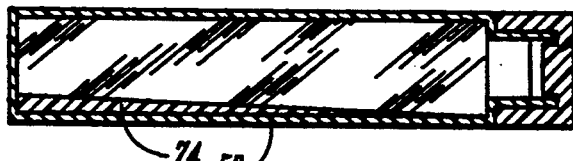
FIG. 9 is a sectional view similar to FIG. 8 but with the embodiment of the invention on its side and showing the cross-sectional gradient of thickness of agar that has been poured into the container.

FIGS. 7 and 8 show the chamber 68 defined by base 52 and cover 62 of case 50. Similarly to the first embodiment, case 50 presents a thin in thickness container which would allow it to be placed in conventional microscopes. The walls of case 50 are transparent and the end 54 can be sealed off by cover 62. As previously described, the exact dimensions can vary. Again, however, thickness of case 50 is in the range of ⅜", and it is preferred that the thickness of this embodiment not exceed ⅜" by very much.

It is also to be understood that in this embodiment the distance between walls 70 and 72, as shown in FIG. 8, is the same. There could be a stepped gradient of thickness from top to bottom, or a sloped gradient of thickness. There also could be flat portions of different sizes and positions relative to one another (compared to stair step type consecutively descending or ascending steps).

It is to be understood that embodiment shown in FIGS. 5–8, with parallel walls, could be used to setup a gradient of thickness of agar 74 in the following way. Case 50 could be held in such a way (tipped from vertical) so that agar 74 poured through opening 56 would spread out along an interior wall. By appropriate tipping of case 50, agar 74 would spread across the wall in a thin cross-section towards opening 56 but would increase in thickness towards the bottom of case 50. By allowing the agar 74 to form in such a wedge-shape (see FIG. 9), the thickness gradient would be created by the way the agar 74 is poured.

E. Embodiment three (FIG. 10)

Figure 10:
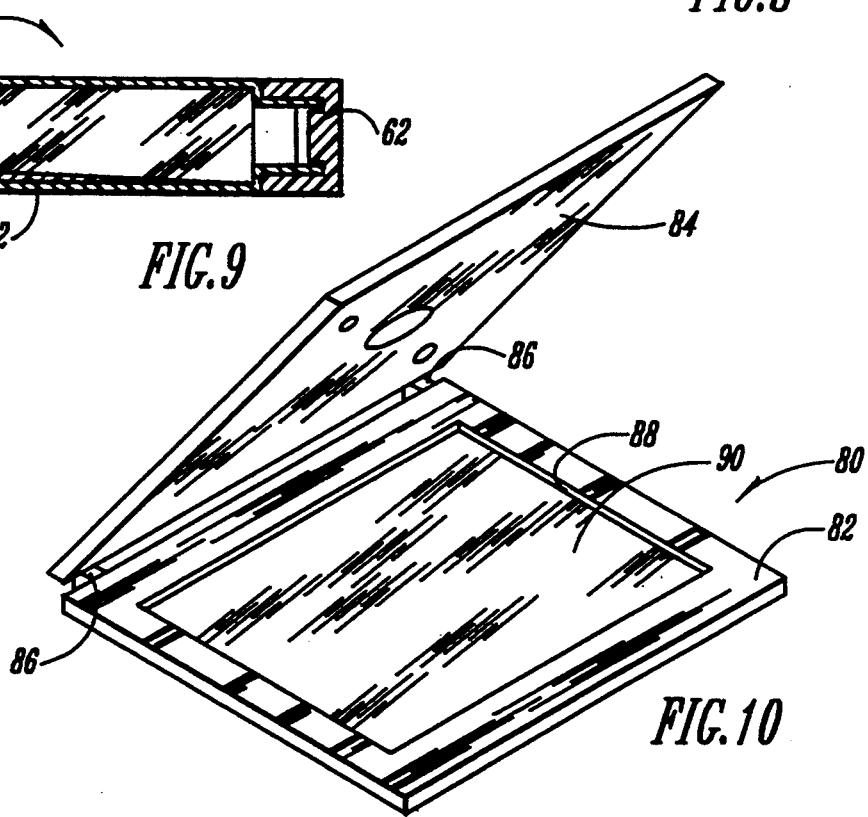
FIG. 10 is a perspective view according to a third embodiment of the present invention.

FIG. 10 shows a third embodiment according to the present invention. A base 82 and cover 84 are connected by hinge 86, similar to the first embodiment. Here, however, cover 84 is generally made of a single thickness flat piece of transparent material. Base 82 is also made of a single piece of flat transparent material with an indentation 88 forming the chamber 90. By closing cover 84 onto base 82, the interfacing surface of cover 84 would abut portions of base 82 surrounding indentation 88 to allow a measure of sealing of chamber 90. Adhesives or a gasket could further facilitate the same. It is to be understood that stain and air ports could be used with cover 84, and other features and advantages of the other embodiments could likewise be utilized with this embodiment. A built-in cover slip, like that in FIG. 1, or conventional cover slips could also be used.

As can be seen, case 80 represents a thin transparent device that could be utilized in a microscope. Either side of case 80 could be viewed in conventional microscopes, especially the thin-in-cross section portion of chamber 90.

The embodiment of FIG. 10 is shown with a very shallow depth of chamber 90. If very shallow, it is probably not recommended and may not be possible to set up a meaningful thickness gradient of agar, either by pouring or by the way in which the floor of chamber 90 is made (sloped or stepped, as possible examples). This does not preclude utilization of a thickness gradient with this type of case, however.

F. Operation

The basic operation of the above described three embodiments has previously been discussed. The options and flexibility of these devices is wide-ranging.

Conventionally, a fluid agar material would initially be introduced into the base of any of these embodiments. To provide a thin layer of agar, the base would be tilted to allow it to run towards one end. Surface adhesion would maintain a thin layer along the upper part of chamber. If there is a sloped or stepped thickness gradient, the remainder of the agar would collect at the bottom.

Samples would then be introduced to the agar. Samples could include skin or nail shavings, or subcultures from other cultured containers, to give a few examples. The samples could be spotted, that is placed at various spaced positions around the agar. Other methods or arrangements are possible.

Each of the embodiments allows easy access to the agar. Such things as a cover slip, such as known in the art, could be placed over the agar.

The cover can then be closed down onto the base and sealed if desired. The case would then be observed for culture growth. Contrary to the state of the art, which most times requires opening of the container to remove a sample to be placed on a slide for microscopic evaluation, the present invention allows use of the case itself as the equivalent of the microscope slide. This allows the culture to be checked at any time and as many times as desired without disruption, destruction, or procedures which might interject materials into the culture which could defeat the validity of the testing or results, Options according to the invention include the ability to introduce stain into the chamber, or introduce air without detrimental results. Such ports are not required for the invention to operate, but are optional.

Any of the cases can be placed on the conventional microscope stages and in conventional microscope caliber's so that the objective of the microscope can be brought down and clearly focused to see the culture. The surfaces and materials of the case are such that they optically provide a device that allows good viewing of the culture and focusing without distortion of culture.

It has been found that contrary to conventional wisdom, the thin cross-sectional area of the case according to the present invention actually promotes and generates faster culture growth than if thicker portions of agar or the like are utilized. Moreover, such a configuration promotes the type of growth that is most beneficial to quick generation of the types of growth needed to identify such things as fungi and molds. The growth occurs upward against the cover and then spreads against the transparent cover surface allowing better observation. Such growth also encourages capillary action when introducing stain into the chamber. Moreover, such structures allow both top and bottom views of the culture.

The thinness of the agar film provides for advantages such as mentioned above. Care must be taken not to expose the film to air too much so as to prevent the film from drying. The case as according to the present invention allow sealing of the chamber to deter drying of the film.

Finally, the optional gradient of thickness of the chamber allows for comparison of cultures in different thicknesses of agar, or other testing procedures in the same container.

A number of fungi were experimentally used with the preferred embodiments. Specific procedures were taken to test the benefits of using a thin layer of agar within a moisture tight container according to the invention. The results ranged from good to excellent. An increase in maturation rate was seen in some but not all of the fungi. The convenience, however, of observing growth without mechanically disrupting the colonies helped accelerate the identification times compared to thick agar petri plates.

A listing of fungi experimentally tested is:

*Trichophyton tonsurans, T. mentagrophytes, Microsporum gypseum, M. nanum, M. canis, M. audounii, M. vanbreuseghemii, Rhizopus sp., Mucor sp., Absidia sp., Wangiella dermatitidis, Phialophora pedrosei Phialophora verrucosa, Sporothrix schenchii, Scedosporium apiospermum, Cladosporum carrionii, Aspergillus niger, Aspergillus fumigatus, Aspergillus flavus, Penicillium sp., Scopulariopsis sp., Coccidioides immitis, Fusarium species, Acremonium sp., Epidermophyton floccosum, Blastomyces dermatitidis.*

Yeast and bacteria experimentally tested were:

*Candida krusei, Candida albicans, Streptomyces sp., Nocardia sp.*

G. Alternatives/Options/Features

The above described preferred embodiment does not limit the invention. Other options, features and advantages are possible.

It is submitted that one skilled in the art will be able to clearly understand the preferred embodiment sufficiently to make and use the invention with this information.

It will be appreciated that the present invention can take many forms and embodiments. The true essence and spirit of the invention are defined in the appended claims, and it is not intended that the embodiments of the invention presented herein should limit the scope thereof.

What is claimed is:

1. A (container) case both for growing and for observing microbiological organisms in situ comprising:
   a housing having a length, width and thickness all of which fit into and can be grasped by a conventional light microscope, the thickness of the housing being on the order of ⅜ inch or less;
   the housing having walls which are transparent, the walls defining an interior chamber allowing view of any contents of the chamber from any view point, and the walls being configurable to make the chamber substantially air tight;
   the chamber including interior upper and lower surfaces defining the cross-sectional area of the chamber; and
   the cross-sectional area varying between the upper and lower surfaces by having a cross-sectional thickness gradient so that all cross-sectional areas of the chamber can be observed by the microscope without modification.

2. The case of claim 1 wherein the housing is substantially rectangular with top and bottom sides which are substantially flat.

3. The case of claim 1 wherein the width and length of the housing are between approximately 60 mm–70 mm and 80 mm–90 mm respectively.

4. The case of claim 1 wherein the walls defining the chamber, at least at one location, are spaced a distance so that the chamber at that location is on the order of 1 mm thick in cross-section.

5. The case of claim 1 wherein one of said walls of the housing is movable between a closed position and an open position to provide access to the chamber.

6. The case of claim 5 further comprising a securement device to securably latch the movable wall over the chamber.

7. The case of claim 5 wherein the moveable wall is hinged to the housing.

8. The case of claim 7 wherein the moveable wall is removeably secured to the housing.

9. The case of claim 1 further comprising an opening to the chamber of at least one half the width of the housing to allow access to the chamber.

10. The case of claim 1 wherein the cross-sectional thickness gradient varies between approximately 1 mm and 4 mm.

11. The case of claim 1 further comprising one or more of an air port, stain port, and built in cover slip positioned on the housing.

12. A case for growing and observing in situ microorganisms grown in a solidifiable growth medium comprising:
   a base having a transparent top surface, the top surface having a first portion in a first plane, a second portion in a second plane, and a third portion in a third plane, the first and second planes being substantially parallel, the third plane connecting adjacent edges of the first and second planes and being oblique to the first and second planes;
   the base having a frame surrounding the top surface to define a basin for holding the solidifiable growth medium and microorganisms;
   a cover having a substantially flat transparent bottom surface and a frame surrounding the bottom surface, the cover being matingly fitable upon the base so that the bottom surface of the cover is closely adjacent and substantially parallel to the first portion of the top and substantially parallel surface of the base, and adjacent but farther away from the second portion of the top surface of the base so that a thin chamber is formed between the top and bottom surfaces of the cover and base and the combined thickness of the cover and base is smaller than needed to allow the case to be positioned in a conventional light microscope without modification to the microscope and the width and length of the combined cover and base can be positioned and held in the conventional light microscope;

the case is made from an optically transparent material;

the top surface of the base and bottom surface of the cover are substantially flat to allow optical viewing without substantial distortion; and a sealing device associated with the base and cover to seal the basin when the cover is closed upon the base.

13. The case of claim 12 wherein the case is substantially rectangular.

14. The case of claim 12 wherein the cover of the base is hinged along an edge of the base.

15. The case of claim 14 further comprising a latching mechanism associated with the opposite edges of the cover and base opposite the hinge.

16. The case of claim 15 wherein the latching mechanism is mechanical and consists of connection members, one each associated with the cover and the base.

17. The case of claim 15 wherein the latching mechanism is an adhesive substance that causes the cover and base to be held together.

18. The case of claim 12 wherein the sealing device includes a gasket.

19. The case of claim 12 wherein the sealing device includes a semi-solid sealant.

20. The case of claim 12 further comprising a stain port in the cover.

21. The case of claim 12 further comprising an air port in the cover.

22. A case for growing and observing in situ microbiological cultures comprising:

a bottom plate defining a chamber;

a thin optically transparent top plate of a dimension to cover said chamber;

the top plate and the bottom plate being releasably interconnected; and the case having a cross-sectional thickness of $\frac{3}{8}$ inch or less so that it can be used to grow a microbiological cuture as well as allow in situ viewing of the culture on a conventional light microscope;

the chamber having a varying cross-sectional area and being formed between the top and bottom plates;

a sealing means to seal the chamber in a substantially air tight manner.

* * * * *

UNITED STATES PATENT AND TRADEMARK OFFICE
CERTIFICATE OF CORRECTION

PATENT NO. : 5,417,576
DATED : May 23, 1995
INVENTOR(S) : Dennis R. Hill

It is certified that error appears in the above-indentified patent and that said Letters Patent is hereby corrected as shown below:

Column 10, line 1 of claim 1, please delete "(container)".

Column 11, line 21 of claim 14, please delete "of the base".

Column 12, line 21 of claim 22, please delete "cuture" and substitute --culture--.

Signed and Sealed this

Third Day of October, 1995

BRUCE LEHMAN

*Attest:*

*Attesting Officer*    Commissioner of Patents and Trademarks